(12) United States Patent
Nogami et al.

(10) Patent No.: US 12,127,553 B2
(45) Date of Patent: Oct. 29, 2024

(54) CELL CRYOPRESERVATION COMPOSITION AND CRYOPRESERVATION METHOD

(71) Applicants: Saraya Co., Ltd., Osaka (JP); Osaka University, Suita (JP)

(72) Inventors: Asuka Nogami, Kashiwara (JP); Motoki Tatsumi, Kashiwara (JP); Nanase Ishii, Kashiwara (JP); Mizuyuki Ryu, Kashiwara (JP); Yoshihiko Hirata, Kashiwara (JP); Yoshiki Sawa, Suita (JP); Shigeru Miyagawa, Suita (JP); Atsuhiro Saito, Suita (JP); Hirotatsu Ohkawara, Suita (JP)

(73) Assignees: SARAYA CO., LTD., Osaka (JP); OSAKA UNIVERSITY, Osaka (JP)

( * ) Notice: Subject to any disclaimer, the term of this patent is extended or adjusted under 35 U.S.C. 154(b) by 343 days.

(21) Appl. No.: 17/664,194

(22) Filed: May 19, 2022

(65) Prior Publication Data
US 2022/0272963 A1    Sep. 1, 2022

Related U.S. Application Data

(62) Division of application No. 16/482,236, filed as application No. PCT/JP2018/002879 on Jan. 30, 2018, now abandoned.

(30) Foreign Application Priority Data

Jan. 31, 2017  (JP) .................................. 2017-016266

(51) Int. Cl.
  *C12N 1/04*   (2006.01)
  *A01N 1/02*   (2006.01)
  *C12N 5/0775* (2010.01)

(52) U.S. Cl.
  CPC ............. *A01N 1/0221* (2013.01); *C12N 1/04* (2013.01); *C12N 5/0663* (2013.01); *C12N 5/0665* (2013.01)

(58) Field of Classification Search
  None
  See application file for complete search history.

(56) References Cited

U.S. PATENT DOCUMENTS

| | | |
|---|---|---|
| 5,118,512 A | 6/1992 | O'Leary et al. |
| 5,580,714 A | 12/1996 | Polovina |
| 5,756,471 A | 5/1998 | Hillion et al. |
| 5,759,764 A | 6/1998 | Polovina |
| 2008/0187593 A1 | 8/2008 | Bluth |
| 2012/0128641 A1 | 5/2012 | Austen |
| 2012/0220464 A1 | 8/2012 | Giessler-Blank et al. |
| 2016/0280733 A1 | 9/2016 | Araki et al. |
| 2017/0014489 A1 | 1/2017 | Suzuki et al. |
| 2018/0020658 A1* | 1/2018 | Campbell .............. C07H 15/06 435/1.3 |

FOREIGN PATENT DOCUMENTS

| | | |
|---|---|---|
| EP | 3 117 838 A1 | 1/2017 |
| JP | H10-511402 A | 11/1998 |
| JP | 2001-247401 A | 9/2001 |
| JP | 2007-106733 A | 4/2007 |
| JP | 2010-158192 A | 7/2010 |
| JP | 2011-030557 A | 2/2011 |
| JP | 2012-232963 A | 11/2012 |
| JP | 2012-235728 A | 12/2012 |
| JP | 5940975 B2 | 12/2012 |
| JP | 2014-117240 A | 6/2014 |
| JP | 5630979 B2 | 11/2014 |
| JP | 2016-160244 A | 9/2016 |
| WO | WO 2004/044216 A1 | 5/2004 |
| WO | WO 2011/011055 A2 | 1/2011 |

OTHER PUBLICATIONS

Kovelock J.E. and Bioshop, M.W.H. 1959 "Prevention of freezing damage to living cells by dimethyl sulphoxide" *Nature* 183: 1394-1395.

Mazur, P. 1984 "Freezing of living cells: mechanisms and implications" *Cell Physiol* 16: C125-C142.

Supplementary European Search Report in European Patent Application No. EP 18 74 7715.3 issued Oct. 12, 2020.

Ishii, Nanase et al., "Transdermal administration of lactoferrin with sophorolipid", Biochem. Cell Biol., vol. 90, No. 3, Jan. 1, 2012, pp. 504-512.

Deckner, George, "Prospector: Humectants: Materials with Multiple Benefits," Jun. 26, 2015.

\* cited by examiner

*Primary Examiner* — Evelyn Y Pyla
(74) *Attorney, Agent, or Firm* — Knobbe Martens Olson & Bear LLP

(57) ABSTRACT

A cell cryopreservation method including adding a 1 volume % of a composition comprising 0.01 wt % to 20 wt % of a sophorose lipid to cells in a cell culture medium just before or up to 6 hours before cryopreserving the cells; and cryopreserving the cell culture medium, wherein the composition improves cell viability after cryopreservation compared to cells that are cryopreserved with a similar composition that does not contain the sophorose lipid.

8 Claims, 3 Drawing Sheets

CELL CRYOPRESERVATION COMPOSITION AND CRYOPRESERVATION METHOD

TECHNICAL FIELD

The present invention relates to cryopreservation compositions that are used to cryopreserve cells, and cryopreservation methods using the same.

BACKGROUND ART

Cell cryopreservation is widely used as an essential technique to prevent cell degeneration due to passaging, prevent contamination with bacteria associated with passaging, transport cells, etc. However, it is known that, in the process of freezing cells, water in and out of the cells turns into ice crystals and the ice crystals damage the cells (Non-Patent Document 1). It I therefore desired to protect cells from damage during freezing and thawing and to cryopreserve cells while maintaining their properties.

In common cryopreservation, cells are typically suspended in a culture solution containing bovine serum etc. with a cryoprotectant for protecting the cells from damage from ice crystals, and the cell suspension thus obtained is placed in a cryotube etc., cooled, and eventually cryopreserved at a cryogenic temperature of −80° C. or −196° C. The cryoprotectant is 5 to 20% of dimethyl sulfoxide (DMSO), glycerin (Gly), ethylene glycol (EG), propylene glycol (PG), etc. (Patent Documents 1, 2). The most effective and most common cryoprotectant among these is DMSO (Non-Patent Document 2). However, a cryopreservation solution containing DMSO as a cryoprotectant does not have satisfactory preservation efficiency, and it cannot necessarily be said that this cryopreservation solution sufficiently inhibits ice crystal formation.

There are a cryopreservation solution further containing polyether to enhance the effect of DMSO (Patent Document 3), a cryopreservation solution containing a fructan to enhance the cytoprotective effect (Patent Document 4), and a cryopreservation solution containing carboxylated polylysine to enhance the stem cell storing effect (Patent Document 5). However, it cannot be said that these cryopreservation solutions sufficiently inhibit ice crystal formation. There is a concern about cytotoxicity of residual polyether, and a less toxic cryopreservation solution is desired. Moreover, since the cryopreservation solution contains as high as 30% of fructan, this is economically disadvantageous, and it is also difficult to remove fructan after preservation. Cell preservation using carboxylated polylysine focuses only on stem cells and is therefore not so versatile. Furthermore, since carboxylated polylysine is a polypeptide, there is also a concern about its impact on cell functionality etc. The above cryopreservation solutions are thus not always satisfactory with respect to cell preservation. Accordingly, a low-toxic cryopreservation solution is desired which can preserve all the cells.

CITATION LIST

Patent Documents

PATENT DOCUMENT 1: Japanese Patent No. 5940975
PATENT DOCUMENT 2: Japanese Unexamined Patent Publication No. 2001-247401
PATENT DOCUMENT 3: Japanese Unexamined Patent Publication (Japanese Translation of PCT Application) No. H10-511402
PATENT DOCUMENT 4: Japanese Unexamined Patent Publication No. 2012-235728
PATENT DOCUMENT 5: Japanese Patent No. 5630979
PATENT DOCUMENT 6: Japanese Unexamined Patent Publication No. 2016-160244

Non-Patent Documents

NON-PATENT DOCUMENT 1: Mazur, Am. J. Physiol., 247:C125-142, 1984
NON-PATENT DOCUMENT 2: Kovelock J E and Bioshop M W H, Nature 183:1394-1395, 1959

SUMMARY OF THE INVENTION

Technical Problem

Since current cryopreservation methods do not sufficiently inhibit ice crystal formation and do not sufficiently protect cells from freezing damage, development of a novel low-toxic cryopreservant is desired.

Solution to the Problem

The inventors intensively studied to solve the above problems and found that a sophorose lipid (SL) can inhibit ice crystal formation and can easily reduce freezing damage to cells. Based on these findings, the inventors found that adding 0.01 wt % to 20 wt % of SL to a cell culture solution before cryopreservation improves cell preservation efficiency and that adding 0.01 wt % to 20 wt % of SL during cryopreservation reduces DMSO toxicity. The inventors also found that mixing 1 wt % to 50 wt % of a polyhydric alcohol with 0.01 wt % to 20 wt % of SL improves cell viability after cryopreservation without adding DMSO. The present invention provides the following:

[1] A composition that contains 0.01 wt % to 20 wt % of a sophorose lipid and improves cell viability after cryopreservation.
[2] The composition of [1], containing 5 wt % to 10 wt % of dimethyl sulfoxide (DMSO).
[3] The composition of [1] or [2], containing 1 wt % to 50 wt % of a polyhydric alcohol.
[4] The composition of [3], containing at least one of glycerin, ethylene glycol, and propylene glycol as the polyhydric alcohol.
[5] A cell cryopreservation method in which 1 volume % of the composition of [1] is added to a cell culture medium just before or up to 6 hours before cryopreserving cells.
[6] A cell cryopreservation method in which 10 volume % to 99 volume % of the composition of any of [2] to [4] is added to a cell culture medium when cryopreserving cells.

Advantages of the Invention

Addition of SL can reduce freezing damage to cells. As a result, a certain level or higher of cell viability can be obtained even without relying on the effects of DMSO and serum.

SL, (C) is 0.1% SL, (D) is 10% DMSO, (E) is 10% Gly, (F) is 10% PG, (G) is 10% EG, and (H) is 10% APG.

Figure 2:
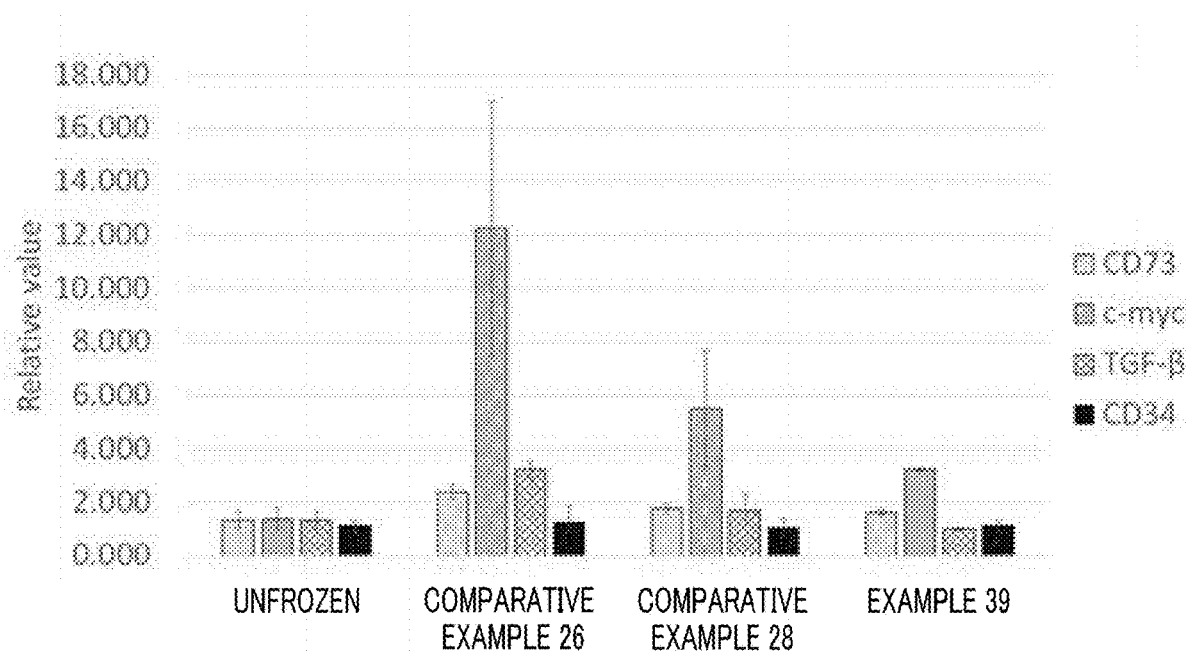

FIG. 2 is a graph showing expression of cell markers.

FIG. 3(A)-(K) are micrographs showing cell morphology, where (A) is 0.2% SL+30% Gly, (B) is 0.2% SL+20% Gly, (C) is 0.2% SL+15% Gly, (D) is 0.1% SL+30% Gly, (E) is 0.1% SL+20% Gly, (F) is 0.1% SL+15% Gly, (G) is 0.05% SL+30% Gly, (H) is 0.05% SL+20% Gly, (I) is 0.05% SL+15% Gly, (J) is 30% Gly, and (K) is 20% DMSO.

DESCRIPTION OF EMBODIMENTS

SL is a low-toxic glycolipid biosurfactant and is a fermentation product produced by fermentation of yeast. SL has the following effects. When added before freezing cells (addition before freezing), SL is taken into the cells and inhibits ice crystal formation within the cells. When added upon freezing, SL inhibits ice crystal formation outside the cells. SL used in the following experimental examples and examples was prepared according to the description in Japanese Unexamined Patent Publication No. 2016-160244. SL adjusted to pH 6 to 8 was used. A pH adjuster is an alkaline agent, an acid, etc.

A polyhydric alcohol is glycerin, ethylene glycol, propylene glycol, etc. and is preferably propylene glycol.

Cells for a cell preservation solution are animal and plant cells such as somatic cells, cancer cells, cell lines, and stem cells.

The cell preservation solution is also similarly applicable to tissues formed by cells, organs, and individuals such as animals and plants. The cell preservation solution can be expected to keep plant- and animal-derived foods fresh.

The freezing and thawing methods using the present invention are not particularly limited. Fine temperature control need not necessarily be performed during freezing, and common slow freezing and rapid thawing may also be used.

EXPERIMENTAL EXAMPLES: ICE CRYSTAL FORMATION INHIBITING COMPOSITION AND ICE CRYSTAL FORMATION INHIBITING EFFECT

Each of the compositions shown in Table 1 was mixed with Dulbecco's modified Eagle's medium (DMEM), which is a medium most commonly used for cell preservation, at a volume ratio of 7:3. Each sample was dispensed into a 15 ml centrifuge tube (Thermo Scientific BioLite) and cooled at 4° C. for 5 minutes, −20° C. for 20 minutes, and −80° C. in this order, and the appearance of each sample was visually observed after cooling at −80° C. for 10 minutes.

TABLE 1

| | Composition | Ice Crystal Formation Inhibiting Effect |
|---|---|---|
| Example 1 | 33 wt % SL | ○ |
| Example 2 | 0.033 wt % SL | ○ |
| Example 3 | 33 wt % APG | ○ |
| Example 4 | 0.033 wt % APG | ○ |
| Example 5 | distilled water or ultrapure water | x |
| Example 6 | 33 wt % DMSO | Δ |

○: No ice crystal seen
Δ: Small ice crystals seen
x: Large ice crystals seen
APG: alkyl polyglucoside*
(*PLANTACARE 200UP, BASF Japan Ltd.)

The results in Table 1 show that Examples 1 to 4 inhibited ice crystal formation more than Examples 5 and 6 did.

Ultrapure water solutions with compositions as shown in Table 2 were prepared. Each sample was frozen by a cooling stage of a scanning probe microscope (AFM5000/AFM5300, Hitachi High-Tech Science Corporation) and observed with an optical microscope. This test was conducted with support of Nanotechnology Open Facilities in Osaka University. Each obtained image was analyzed using image analysis software (OLYMPUS cellSens Standard) to measure the area per ice crystal.

TABLE 2

| Composition | Ice Crystal Area ($\mu m^2$) |
|---|---|
| Ultrapure Water | 307.3 |
| 10 wt % SL | 1.6 |
| 0.1 wt % SL | 1.8 |
| 10 wt % DMSO | 4.2 |
| 10 wt % Gly | 4.8 |
| 10 wt % PG | 3.3 |
| 10 wt % EG | 4.4 |
| 10 wt % APG | 1.8 |

Figure 1:
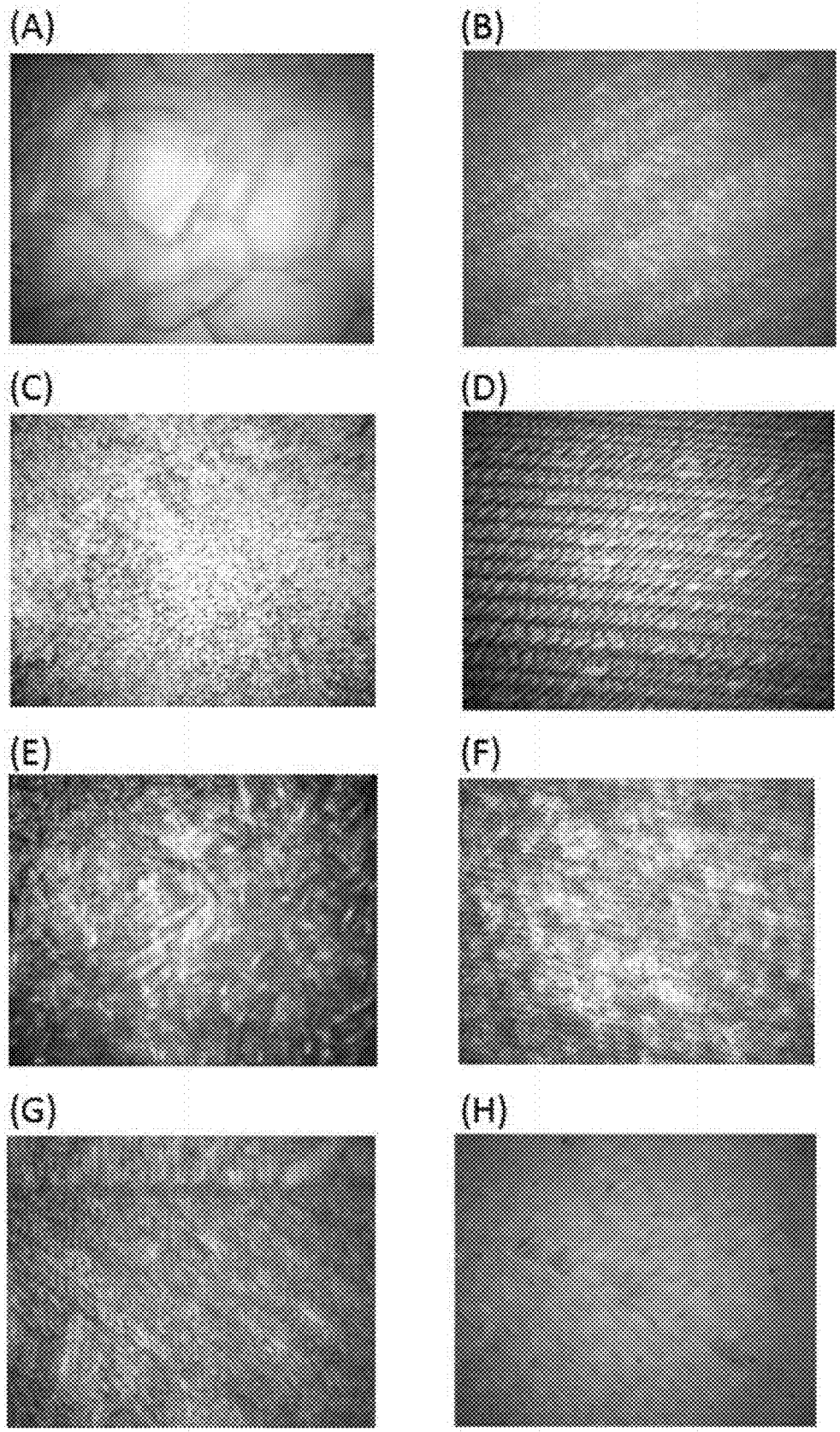
FIG. 1(A)-(H) are micrographs showing inhibition of ice crystal formation, where (A) is ultrapure water, (B) is 10%

* SL: sophorose lipid
Gly: glycerin
EG: ethylene glycol
PG: propylene glycol
APG: alkyl polyglucoside FIG. 1, (A)-(H) are micrographs showing inhibition of ice crystal formation, where (A) is ultrapure water, (B) is 10 wt % SL, (C) is 0.1 wt % SL, (D) is 10 wt % DMSO, (E) is 10 wt % Gly, (F) is 10 wt % PG, (G) is 10 wt % EG, and (H) is 10 wt % APG. As shown in FIGS. 1B and 1C, the solutions containing SL inhibited ice crystal formation regardless of whether the SL content was 0.1 wt % or 10 wt %. As shown in FIGS. 1, (A), (D), (E), (F) and (G), ultrapure water and the solutions containing a substance other than SL did not sufficiently inhibit ice crystal formation. As shown in FIG. 1, (H), however, the solution containing APG that is the same glycolipid surfactant as SL inhibited ice crystal formation.

EXAMPLES

[1. Effect of SL Addition Upon Culturing Before Cryopreservation (Human Normal Fibroblasts, Serum-Containing Medium)]

Human normal fibroblasts (KURABO) were sown on a 6-well plate at $3.2 \times 10^4$ cells/ml and cultured for 48 hours. After culturing, the culture medium was removed, and a 5 wt % SL aqueous solution was diluted with DMEM containing fetal bovine serum to prepare a 0.05 volume % SL solution. The solution thus prepared was added to the cultured cells. After culturing for a predetermined time, the viable cell count was measured by trypan blue staining (viable cell count before freezing). The remaining cells were suspended in 1 ml of a 10% DMSO/fetal bovine serum-containing DMEM solution in CRYOGENIC VIAL (Sansyo Co., Ltd.), and the cell suspension thus obtained was cooled at 4° C. for 5 minutes, −20° C. for 20 minutes, and −80° C. in this order. After overnight storage at −80° C., the cell suspension was rapidly thawed at 37° C., and the viable cell count was measured by trypan blue staining (viable cell count after thawing). The remaining cell suspension was sown on a 6-well plate and the cells were cultured for 72 hours. The viable cell count after culturing was measured by trypan blue staining (viable cell count after culturing).

The viability upon thawing and the proliferation rate were calculated by the following equations.

Viability upon thawing (%)=viable cell count after thawing/total cell count after thawing×100

Proliferation rate (%)=viable cell count after culturing/viable cell count after thawing×100

TABLE 3

| Sample | | Viability Upon Thawing (%) | Proliferation Rate (%) |
|---|---|---|---|
| Comparative Example 1 | Not added | 86.7 | 467.8 |
| Example 1 | Added 1 hr before cell recovery | 91.4 | 570.5 |
| Example 2 | Added 4 hrs before cell recovery | 90.1 | 753.5 |
| Example 3 | Added 6 hrs before cell recovery | 94.9 | 741.6 |

The results in Table 3 show culturing with SL added 1 to 6 hours before cell cryopreservation resulted in higher cell viability upon thawing and a higher cell proliferation rate than culturing with no SL added.

Not only the viability upon thawing but also the viability before and after freezing were examined Specifically, human normal fibroblasts (KURABO) were sown on a 10 mm dish at $4.0 \times 10^4$ cells/ml and cultured for 72 hours. After culturing, a 5 wt % SL aqueous solution was diluted to prepare a 0.05 volume % SL solution, and the solution thus prepared was added to the cultured cells. After culturing for a predetermined time, the resultant cell suspension was sown on a 96-well plate at $2.0 \times 10^4$ cells/ml, and the cells were cultured for 6 or 72 hours. Absorbance was then measured with Cell Counting Kit-8 (DOJINDO LABORATORIES) (absorbance before freezing). The remaining cells were suspended at a cell density of $4.0 \times 10^5$ cells/ml, and the cell suspension thus prepared and 20% DMSO were mixed at a volume ratio of 1:1 in CRYOGENIC VIAL (Sansyo Co., Ltd.). The resultant cell suspension was placed in a freezing container, BICELL (Nihon Freezer Co., Ltd.), and cooled at −80° C. After overnight storage, the cell suspension was rapidly thawed at 37° C., 100 μl of the cell suspension was sown on a 96-well plate, and the cells were cultured for 6 or 72 hours. Absorbance was then measured with Cell Counting Kit-8 (DOJINDO LABORATORIES) (absorbance after cryopreservation).

The viability before and after freezing and the proliferation rate were calculated by the following equations.

Viability before and after freezing (%)=absorbance after cryopreservation (6-hour culture)/absorbance before freezing (6-hour culture)

Proliferation rate (%)=absorbance after cryopreservation (72-hour culture)/absorbance before freezing (72-hour culture)

TABLE 4

| Sample | | Viability (%) | Proliferation Rate (%) |
|---|---|---|---|
| Comparative Example | Not added | 60.7 | 93.4 |
| Example 27 | Added 1 hr before cell recovery | 77.4 | 102.0 |
| Example 28 | Added 4 hrs before cell recovery | 79.2 | 98.8 |
| Example 29 | Added 6 hrs before cell recovery | 82.7 | 96.4 |

The results in Table 4 show that culturing with SL added 1 to 6 hours before cell cryopreservation resulted in higher cell viability before and after freezing and a higher cell proliferation rate than culturing with no SL added.

[2. Effect of SL Addition Upon Culturing Before Cryopreservation (Human Normal Fibroblasts, Serum-Free Medium)]

Human normal fibroblasts (KURABO) were sown on a 6-well plate at $3.2 \times 10^4$ cells/ml and cultured for 48 hours. After culturing, the culture medium was removed, and a 5 wt % SL aqueous solution was diluted with a DMEM medium to prepare a 0.05 volume % SL solution. The solution thus prepared was added to the cultured cells. After culturing for 6 hours, the viable cell count was measured by trypan blue staining (viable cell count before freezing). The remaining cells were suspended in 1 ml of a 10% DMSO/DMEM solution in CRYOGENIC VIAL (Sansyo Co., Ltd.), and the cell suspension thus obtained was cooled at 4° C. for 5 minutes, −20° C. for 20 minutes, and −80° C. in this order. After overnight storage at −80° C., the cell suspension was rapidly thawed at 37° C., and the viable cell count was measured by trypan blue staining (viable cell count after thawing).

The viability before and after freezing was calculated by the following equation.

Viability before and after freezing (%)=viable cell count after thawing/viable cell count before freezing×100

TABLE 5

| Sample | | Viability Before and After Freezing (%) |
|---|---|---|
| Comparative Example 2 | Not added | 74.3 |
| Example 4 | Added 6 hrs before cell recovery | 97.0 |

The results in Table 5 show that culturing with SL added 6 hours before cell cryopreservation resulted in higher cell viability before and after freezing than culturing with no SL added.

[3. Effect of SL Addition Upon Culturing Before Cryopreservation (Mesenchymal Stem Cells, Serum-Free Medium)]

Mesenchymal stem cells (Lonza) were sown on a 6-well plate at $3.2 \times 10^4$ cells/ml and cultured for 48 hours. After culturing, the culture medium was removed, and a 5 wt % SL aqueous solution was diluted with an MSCGM-CD medium to prepare a 0.05 volume % SL solution. The solution thus prepared was added to the cultured cells. After culturing for 6 hours, the viable cell count was measured by trypan blue staining (viable cell count before freezing). The remaining cells were suspended in 1 ml of a 10% DMSO/MSCGM-CD medium in CRYOGENIC VIAL (Sansyo Co., Ltd.), and the cell suspension thus obtained was cooled at 4° C. for 5 minutes, −20° C. for 20 minutes, and −80° C. in this order. After overnight storage at −80° C., the cell suspension was rapidly thawed at 37° C., and the viable cell count was measured by trypan blue staining (viable cell count after thawing).

The viability before and after freezing was calculated by the following equation.

Viability before and after freezing (%)=viable cell count after thawing/viable cell count before freezing×100

TABLE 6

| Sample | | Viability Before and After Freezing (%) |
|---|---|---|
| Comparative Example 3 | Not added | 84.3 |
| Example 5 | Added 6 hrs before cell recovery | 94.5 |

The results in Table 6 show that culturing with SL added 6 hours before cell cryopreservation resulted in higher cell viability before and after freezing than culturing with no SL added.

[4. Effect of SL Addition without Culturing Before Cryopreservation (Human Normal Fibroblasts, Serum-Containing Medium)]

The viable cell count of human normal fibroblasts (KURABO) was measured by trypan blue staining (viable cell count before freezing). The cells were suspended in DMEM containing fetal bovine serum. Each of the samples shown in Tables 7 and 8 and the cell suspension were mixed at a volume ratio of 3:7 in CRYOGENIC VIAL (Sansyo Co., Ltd.), and each of the resultant cell suspensions was cooled at 4° C. for 5 minutes, −20° C. for 20 minutes, and −80° C. in this order. After overnight storage at −80° C., each cell suspension was rapidly thawed at 37° C., and the viable cell count was measured by trypan blue staining (viable cell count after thawing). Each of the remaining cell suspensions was sown on a 6-well plate and the cells were cultured for 72 hours. The viable cell count after culturing was measured by trypan blue staining (viable cell count after culturing).

The viability before and after freezing and the proliferation rate was calculated by the following equations.

Viability before and after freezing (%)=viable cell count after thawing/viable cell count before freezing×100

Proliferation rate (%)=viable cell count after culturing/viable cell count after thawing×100

TABLE 7

| | Concentrations and Components | Viability Before and After Freezing (%) |
|---|---|---|
| Example 7 | 0.033 wt % SL + 3.3 wt % Gly | 5.9 |
| Example 8 | 0.033 wt % SL + 16.5 wt % Gly | 39.8 |
| Example 9 | 0.033 wt % SL + 33 wt % Gly | 73.9 |
| Example 10 | 0.033 wt % SL | 5.4 |
| Example 11 | 0.033 wt % SL + 3.3 wt % PG | 7.1 |
| Example 12 | 0.033 wt % SL + 16.5 wt % PG | 71.4 |
| Example 13 | 0.033 wt % SL + 33 wt % PG | 100.0 |
| Comparative Example 4 | 33 wt % DMSO | 84.8 |
| Comparative Example 5 | 33 wt % Gly | 68.9 |
| Comparative Example 6 | 33 wt % PG | 54.9 |

Gly: glycerin (concentrated glycerin, made by Acidchem)
PG: propylene glycol (made by ADEKA CORPORATION)

The results in Table 7 show that Examples 12 and 13 had high cell viability and Example 13 had higher viability than Comparative Examples 4 to 6.

TABLE 8

| | Concentrations and Components | Proliferation Rate (%) |
|---|---|---|
| Comparative Example 7 | 2.2% carboxylated polylysine* | 69.2 |
| Example 14 | 0.033 wt % SL + 16.5 wt % PG | 484.6 |

(*CryoScarless DMSO-Free, made by BioVerde)

Example 14 had a higher proliferation rate than Comparative Example 7.

Human normal fibroblasts were sown on a 96-well plate at $2.0 \times 10^4$ cells/ml and cultured for 6 or 72 hours. After culturing, absorbance was measured with Cell Counting Kit-8 (DOJINDO LABORATORIES) (absorbance before freezing). The remaining cells were suspended at $4.0 \times 10^5$ cells/ml in DMEM containing fetal bovine serum. Each of the compositions shown in Table 9 and the cell suspension were mixed at a volume ratio of 1:1 in CRYOGENIC VIAL (Sansyo Co., Ltd.). Each of the resultant cell suspensions was placed in a freezing container, BICELL (Nihon Freezer Co., Ltd.), and cooled at −80° C. After overnight storage, each cell suspension was rapidly thawed at 37° C., 100 μl of each cell suspension was sown on a 96-well plate, and the cells were cultured for 6 or 72 hours. Absorbance was then measured with Cell Counting Kit-8 (DOJINDO LABORATORIES) (absorbance after cryopreservation).

The viability and the proliferation rate were calculated by the following equations.

Viability (%)=absorbance after cryopreservation (6-hour culture)/absorbance before freezing (6-hour culture)

Proliferation rate (%)=absorbance after cryopreservation (72-hour culture)/absorbance before freezing (72-hour culture)

TABLE 9

| | Concentrations and Components | Viability (%) | Proliferation Rate (%) |
|---|---|---|---|
| Comparative Example 14 | 20 wt % DMSO | 66.5 | 95.9 |
| Comparative Example 15 | 30 wt % Gly | 59.5 | 60.8 |
| Comparative Example 16 | 20 wt % Gly | 53.0 | 54.7 |
| Comparative Example 17 | 15 wt % EG | 65.4 | 70.3 |
| Comparative Example 18 | 15 wt % PG | 77.6 | 81.6 |
| Comparative Example 19 | CELLBANKER*[1] | 86.6 | 101.3 |
| Comparative Example 20 | Reprocryo*[2] | 81.4 | 95.5 |
| Comparative Example 21 | CryoScarless*[3] | 65.3 | 24.4 |
| Comparative Example 22 | BAMBANKER*[4] | 83.5 | 91.9 |
| Comparative Example 23 | CP-5E*[5] | 73.9 | 89.7 |
| Comparative Example 24 | CP-1*[6] | 34.8 | 75.4 |
| Example 30 | 0.02 wt % SL + 30 wt % Gly | 84.6 | 97.3 |
| Example 31 | 0.02 wt % SL + 30 wt % EG | 72.1 | 95.9 |
| Example 32 | 0.02 wt % SL + 30 wt % PG | 54.2 | 85.8 |
| Example 33 | 0.086 wt % SL + 10 wt % Gly + 10 wt % PG + 6.6 wt % EG | 71.9 | 102.8 |
| Example 34 | 0.1 wt % SL + 30 wt % Gly | 82.8 | 94.9 |
| Example 35 | 0.1 wt % SL + 30 wt % EG | 52.7 | 88.8 |
| Example 36 | 0.11 wt % SL + 15 wt % Gly + 15 wt % PG | 72.8 | 104.8 |
| Example 37 | 0.11 wt % SL + 15 wt % Gly + 10 wt % EG | 71.5 | 102.1 |

*[1] STEM-CELLBANKER DMSO Free GMP Grade (Manufacturer: ZENOAQ RESOURCE CO., LTD., Use: human IPS and ES cells)
*[2] ReproCryo DMSO Free RM (Manufacturer: ReproCELL Inc., Use: human IPS and ES cells)
*[3] CryoScarless DMSO-Free (Manufacturer: BioVerde, Use: unspecified)
*[4] BAMBANKER (Manufacturer: GC LYMPHOTEC Inc., Use: human-derived cells)
*[5] CP-5E (Manufacturer: KYOKUTO PHARMACEUTICAL INDUSTRIAL CO., LTD, Use: human IPS and ES cells)
*[6] CP-1 (Manufacturer: KYOKUTO PHARMACEUTICAL INDUSTRIAL CO., LTD, Use: hematopoietic stem cells)

The results in Table 9 confirmed that the examples of the present invention had high cell viability and high cell proliferation rates.

[5. Impact of DMSO Addition on SL Addition without Culturing Before Cryopreservation (Rat Skeletal Muscle Myoblasts, Serum-Containing Medium)]

The viable cell count of rat skeletal muscle myoblasts (JCRB9081 L6) was measured (viable cell count before freezing). The remaining cells were suspended in DMEM containing fetal bovine serum. Each of the compositions shown in Table 7 and the cell suspension were mixed at a volume ratio of 3:7 in CRYOGENIC VIAL (Sansyo Co., Ltd.), and each of the resultant cell suspensions was cooled at 4° C. for 5 minutes, −20° C. for 20 minutes, and −80° C. in this order. After overnight storage at −80° C., each cell suspension was rapidly thawed at 37° C., and the viable cell count was measured (viable cell count after thawing).

The viability was calculated by the following equation.

Viability before and after freezing (%)=viable cell count after thawing/viable cell count before freezing×100

As a property of myoblasts, cytokines (VEGF) in the culture supernatant after 5 days of culture was quantified by ELISA.

TABLE 10

| | Concentrations and Components | Viability Before and After Breezing (%) | VEGF (pg/ml) |
|---|---|---|---|
| Comparative Example 8 | 33 wt % DMSO | 38.0 | 2100 |
| Example 15 | 3.3 wt % SL + 33 wt % DMSO | 10.0 | 3900 |
| Example 16 | 0.33 wt % SL + 33 wt % DMSO | 35.0 | 3400 |
| Example 17 | 0.033 wt % SL + 33 wt % DMSO | 48.0 | 2400 |

The results in Table 10 show that Examples 15 to 17 had higher cell viability than Comparative Example 8 (10 wt % DMSO only) and that Examples 15 to 17 had larger amounts of VEGF than Comparative Example 8 (10 wt % DMSO only). This means that the impact of freezing on cell properties was smaller in the examples than in the comparative example.

[6. Impact of DMSO Addition on SL Addition without Culturing Before Cryopreservation (Human Skeletal Muscle Myoblasts, Serum-Containing Medium)]

The viable cell count of human skeletal muscle myoblasts (from patients) was measured (viable cell count before freezing). The remaining cells were suspended in DMEM containing fetal bovine serum. Each of the compositions shown in Table 11 and the cell suspension were mixed at a volume ratio of 3:7 in CRYOGENIC VIAL (Sansyo Co., Ltd.), and each of the resultant cell suspensions was cooled at 4° C. for 5 minutes, −20° C. for 20 minutes, and −80° C. in this order. After overnight storage at −80° C., each cell suspension was rapidly thawed at 37° C., and the viable cell count was measured (viable cell count after thawing).

The viability was calculated by the following equation.

Viability before and after freezing (%)=viable cell count after thawing/viable cell count before freezing×100

TABLE 11

| | Concentrations and Components | Viability Before and After Freezing (%) |
|---|---|---|
| Comparative Example 9 | 33 wt % DMSO | 81.5 |
| Example 18 | 33 wt % SL + 33 DMSO | 90.7 |
| Example 19 | 3.3 wt % SL + 33% DMSO | 93.4 |
| Example 20 | 0.33 wt % SL+ 33% DMSO | 95.5 |
| Example 21 | 0.033 wt % SL + 33% DMSO | 93.6 |

DMSO: made by FUJIFILM Wako Pure Chemical Corporation

The results in Table 11 show that Examples 18 to 21 had higher cell viability than Comparative Example 9 (10 wt % DMSO only).

The impact of DMSO addition on SL addition regarding viability upon thawing was examined by using Caco-2 cells and a serum-containing medium. Specifically, the viable cell count of Caco-2 cells (human colon adenocarcinoma) was measured (viable cell count before freezing). The remaining cells were suspended in DMEM containing fetal bovine serum. Each of the compositions shown in Table 10 and the cell suspension were mixed at a volume ratio of 1:1 in CRYOGENIC VIAL (Sansyo Co., Ltd.), and each of the resultant cell suspensions was cooled at 4° C. for 5 minutes, −20° C. for 20 minutes, and −80° C. in this order. After overnight storage at −80° C., each cell suspension was rapidly thawed at 37° C., and the viable cell count was measured (viable cell count after thawing).

The viability was calculated by the following equation.

Viability upon thawing (%)=viable cell count after thawing/total cell count after thawing×100

TABLE 12

| | Concentrations and Components | Viability Upon Thawing (%) |
|---|---|---|
| Comparative Example 25 | 20 wt % DMSO | 86.0 |
| Example 38 | 0.02 wt % SL + 20 wt % DMSO | 90.0 |

The results in Table 12 show that the example of the present invention had higher viability upon thawing than the comparative example (20 wt % DMSO only).

[7. Impact of PG Addition on SL Addition without Culturing Before Cryopreservation (Human Normal Fibroblasts, Serum-Free Medium)]

The viable cell count of human normal fibroblasts (KURABO) was measured by trypan blue staining (viable cell count before freezing). The cells were suspended in serum-free DMEM. Each of the samples shown in Table 13 and the cell suspension were mixed at a volume ratio of 3:7 in CRYOGENIC VIAL (Sansyo Co., Ltd.), and each of the resultant cell suspensions was cooled at 4° C. for 5 minutes, −20° C. for 20 minutes, and −80° C. in this order. After overnight storage at −80° C., each cell suspension was rapidly thawed at 37° C., and the viable cell count was measured by trypan blue staining (viable cell count after thawing).

The viability before and after freezing and the viability after proliferation were calculated by the following equations.

Viability before and after freezing (%)=viable cell count after thawing/viable cell count before freezing×100

Viability after proliferation (%)=viable cell count after culturing/total cell count after culturing×100

TABLE 13

| | Concentrations and Components | Viability Before and After Freezing (%) | Viability After Proliferation (%) |
|---|---|---|---|
| Example 22 | 0.033 wt % SL + 16.5 wt % PG | 50.2 | 76.5 |
| Example 23 | 0.033 wt % SL + 33 wt % PG | 60.2 | 100.0 |
| Comparative Example 10 | 33 wt % PG | 34.4 | 95.8 |
| Comparative Example 11 | 33 wt % DMSO | 61.0 | 97.1 |

The results in Table 13 show that Examples 22 and 23 had higher viability before and after freezing than Comparative Example 10 and that Example 23 had higher viability after proliferation than Comparative Examples 10 and 11.

[8. Impact of PG Addition on SL Addition without Culturing Before Cryopreservation (Mesenchymal Stem Cells, Serum-Free Medium)]

The viable cell count of mesenchymal stem cells (Lonza) was measured by trypan blue staining (viable cell count before freezing). The cells were suspended in an MSCGM-CD medium. Each of the samples shown in Table 14 and the cell suspension were mixed at a volume ratio of 3:7 in CRYOGENIC VIAL (Sansyo Co., Ltd.), and each of the resultant cell suspensions was cooled at 4° C. for 5 minutes, −20° C. for 20 minutes, and −80° C. in this order. After overnight storage at −80° C., each cell suspension was rapidly thawed at 37° C., and the viable cell count was measured by trypan blue staining (viable cell count after thawing).

The viability before and after freezing was calculated by the following equation.

Viability before and after freezing (%)=total cell count after thawing/total cell count before freezing×100

TABLE 14

| | Concentrations and Components | Viability Before and After Freezing (%) |
|---|---|---|
| Example 24 | 0.033 wt % SL + 3.3 wt % PG | 88.1 |
| Example 25 | 0.033 wt % SL + 16.5 wt % PG | 90.3 |
| Example 26 | 0.033 wt % SL + 33 wt % PG | 92.6 |
| Comparative Example 12 | 33 wt % PG | 83.9 |
| Comparative Example 13 | 33 wt % DMSO | 89.2 |

The results in Table 14 show that Examples 24 to 26 had higher viability before and after freezing than Comparative Example 12 and that Examples 25 and 26 had higher viability before and after freezing than Comparative Example 13.

The impact of addition of a polyhydric alcohol other than PG on SL addition without culturing before cryopreservation (mesenchymal stem cells, serum-containing medium) was also examined Specifically, mesenchymal stem cells (Lonza) were sown on a 96-well plate at $2.0 \times 10^4$ cells/ml and cultured for 6 or 72 hours. After culturing, absorbance was measured with Cell Counting Kit-8 (DOJINDO LABORATORIES) (absorbance before freezing). The remaining cells were suspended at $4.0 \times 10^5$ cells/ml in DMEM containing fetal bovine serum. Each of the compositions shown in Table 15 and the cell suspension were mixed at a volume ratio of 1:1 in CRYOGENIC VIAL (Sansyo Co., Ltd.). Each of the resultant cell suspensions was placed in a freezing container, BICELL (Nihon Freezer Co., Ltd.), and cooled at −80° C. After overnight storage, each cell suspension was rapidly thawed at 37° C., 100 µl of each cell suspension was sown on a 96-well plate, and the cells were cultured for 6 or 72 hours. Absorbance was then measured with Cell Counting Kit-8 (DOJINDO LABORATORIES) (absorbance after cryopreservation). Cellular gene (mRNA) expression before and after freezing was also evaluated.

The viability and the proliferation rate were calculated by the following equations.

Viability (%)=absorbance after cryopreservation (6-hour culture)/absorbance before freezing (6-hour culture)

Proliferation rate (%)=absorbance after cryopreservation (72-hour culture)/absorbance before freezing (72-hour culture)

TABLE 15

| | Concentrations and Components | Viability (%) | Proliferation Rate (%) |
|---|---|---|---|
| Example 39 | 0.01 wt % SL + 20 wt % Gly | 60.6 | 71.6 |
| Example 40 | 0.02 wt % SL + 30 wt % Gly | 37.7 | 67.6 |
| Example 41 | 0.02 wt % SL + 30 wt % EG | 30.6 | 62.5 |
| Example 42 | 0.1 wt % SL + 30 wt % Gly | 54.3 | 83.7 |
| Example 43 | 0.1 wt % SL + 20 wt % Gly | 71.9 | 74.3 |
| Example 44 | 0.2 wt % SL + 20 wt % Gly | 51.7 | 73.9 |
| Comparative Example 26 | 20 wt % DMSO | 44.7 | 30.7 |
| Comparative Example 27 | 30 wt % Gly | 55.1 | 51.9 |
| Comparative Example 28 | 20 wt % Gly | 54.9 | 34.7 |

The results in Table 15 show that the examples of the present invention had high viability before and after freezing and high proliferation rates before and after freezing, but the viability before and after freezing was slightly lower in the example in which 0.2 wt % of SL was added.

Gene expression of cells was examined for the example of 0.02 wt % SL+30 wt % Gly, the example of 0.02 wt % SL+30 wt % EG, and the example of 0.1 wt % SL+30 wt % Gly of the present invention and the comparative example of 20 wt % DMSO. The results are shown in FIG. 2. CD34 and CD73 are markers of mesenchymal stem cells. There is almost no variation in CD34 and CD73 between the example of the present invention and the unfrozen cells, and the example of the present invention is considered to maintain properties as mesenchymal stem cells. Moreover, there is variation in c-myc, which is an oncogene acting as an accelerator of cell division, between Comparative Example 26 (20 wt % DMSO) and the unfrozen cells, but there is almost no variation in c-myc between the example of the present invention and the unfrozen cells, and the example of the present invention is considered to hardly affect mesenchymal stem cells.

[9. Cytotoxicity of Compositions (Mesenchymal Stem Cells)]

Mesenchymal stem cells (Lonza) were sown on a 96-well plate at $2.0 \times 10^4$ cells/ml and cultured for 72 hours. After culturing, the culture medium was removed, and each of the compositions shown in Table 16 was diluted to the concentration(s) shown in Table 16 with DMEM not containing fetal bovine serum. Each of the solutions thus prepared was added to the cultured cells. After culturing for 48 hours, absorbance was measured with Cell Counting Kit-8 (DO-JINDO LABORATORIES).

The viability was calculated by the following equation.

Viability (%)=absorbance after exposure to composition/absorbance before treatment

TABLE 16

|  | Concentrations and Components | Viability (%) |
|---|---|---|
| Comparative Example 29 | 15 wt % Gly | 62.5 |
| Comparative Example 30 | 10 wt % Gly | 76.7 |
| Comparative Example 31 | 7.5 wt % Gly | 87.8 |
| Comparative Example 32 | 5 wt % Gly | 88.0 |
| Example 45 | 0.025 wt % SL + 10 wt % Gly | 84.0 |
| Example 46 | 0.025 wt % SL + 7.5 wt % Gly | 94.3 |
| Example 47 | 0.025 wt % SL + 5 wt % Gly | 95.5 |
| Example 48 | 0.025 wt % SL | 104.3 |
| Example 49 | 0.05 wt % SL + 15 wt % Gly | 76.0 |
| Example 50 | 0.05 wt % SL + 10 wt % Gly | 88.4 |
| Example 51 | 0.05 wt % SL + 7.5 wt % Gly | 94.3 |
| Example 52 | 0.05 wt % SL + 5 wt % Gly | 91.3 |
| Example 53 | 0.05 wt % SL | 100.8 |
| Example 54 | 0.075 wt % SL + 15 wt % Gly | 80.4 |
| Example 55 | 0.075 wt % SL + 10 wt % Gly | 89.8 |
| Example 56 | 0.075 wt % SL + 7.5 wt % Gly | 97.3 |
| Example 57 | 0.075 wt % SL + 5 wt % Gly | 97.9 |
| Example 58 | 0.075 wt % SL | 105.1 |
| Example 59 | 0.1 wt % SL + 15 wt % Gly | 68.9 |
| Example 60 | 0.1 wt % SL + 10 wt % Gly | 82.1 |
| Example 61 | 0.1 wt % SL + 7.5 wt % Gly | 85.0 |
| Example 62 | 0.1 wt % SL+ 5 wt % Gly | 90.6 |
| Example 63 | 0.1 wt % SL | 96.7 |
| Comparative Example 33 | 10 wt % DMSO | 75.2 |

The results in Table 16 show that the combination of SL and glycerin is less toxic to mesenchymal stem cells than DMSO.

[10. Results of Culturing without Removing Cryopreservation Composition after Thawing (Mesenchymal Stem Cells)]

Mesenchymal stem cells (Lonza) were sown on a 96-well plate at $2.0 \times 10^4$ cells/ml and cultured for 6 or 72 hours. After culturing, absorbance was measured with Cell Counting Kit-8 (DOJINDO LABORATORIES) (absorbance before freezing). The remaining cells were suspended at $4.0 \times 10^5$ cells/ml in DMEM containing fetal bovine serum. Each of the compositions shown in Table 17 and the cell suspension were mixed at a volume ratio of 1:1 in CRYOGENIC VIAL (Sansyo Co., Ltd.). Each of the resultant cell suspensions was placed in a freezing container, BICELL (Nihon Freezer Co., Ltd.), and cooled at −80° C. After overnight storage, each cell suspension was rapidly thawed at 37° C., 100 μl of each cell suspension was sown on a 96-well plate without removing the composition, and the cells were cultured for 6 hours. Absorbance was then measured with Cell Counting Kit-8 (DOJINDO LABORATORIES) (absorbance after cryopreservation).

The viability and the proliferation rate were calculated by the following equations.

Viability (%)=absorbance after cryopreservation (6-hour culture)/absorbance before freezing (6-hour culture)

TABLE 17

|  | Concentrations and Components | Viability (%) | Observed Morphology |
|---|---|---|---|
| Example 64 | 0.2 wt % SL + 30 wt % Gly | 33.9 | Δ |
| Example 65 | 0.2 wt % SL + 20 wt % Gly | 41.7 | ○ |
| Example 66 | 0.2 wt % SL + 15 wt % Gly | 28.0 | ○ |
| Example 67 | 0.1 wt % SL + 30 wt % Gly | 28.2 | Δ |
| Example 68 | 0.1 wt % SL + 20 wt % Gly | 48.6 | ○ |
| Example 69 | 0.1 wt % SL + 15 wt % Gly | 48.7 | ○ |
| Example 70 | 0.05 wt % SL + 30 wt % Gly | 31.9 | Δ |
| Example 71 | 0.05 wt % SL + 20 wt % Gly | 35.0 | ○ |
| Example 72 | 0.05 wt % SL + 15 wt % Gly | 52.7 | ○ |
| Comparative Example 34 | 30 wt % Gly | 20.7 | Δ |
| Comparative Example 36 | 20 wt % DMSO | 10.8 | x |

Figure 3:
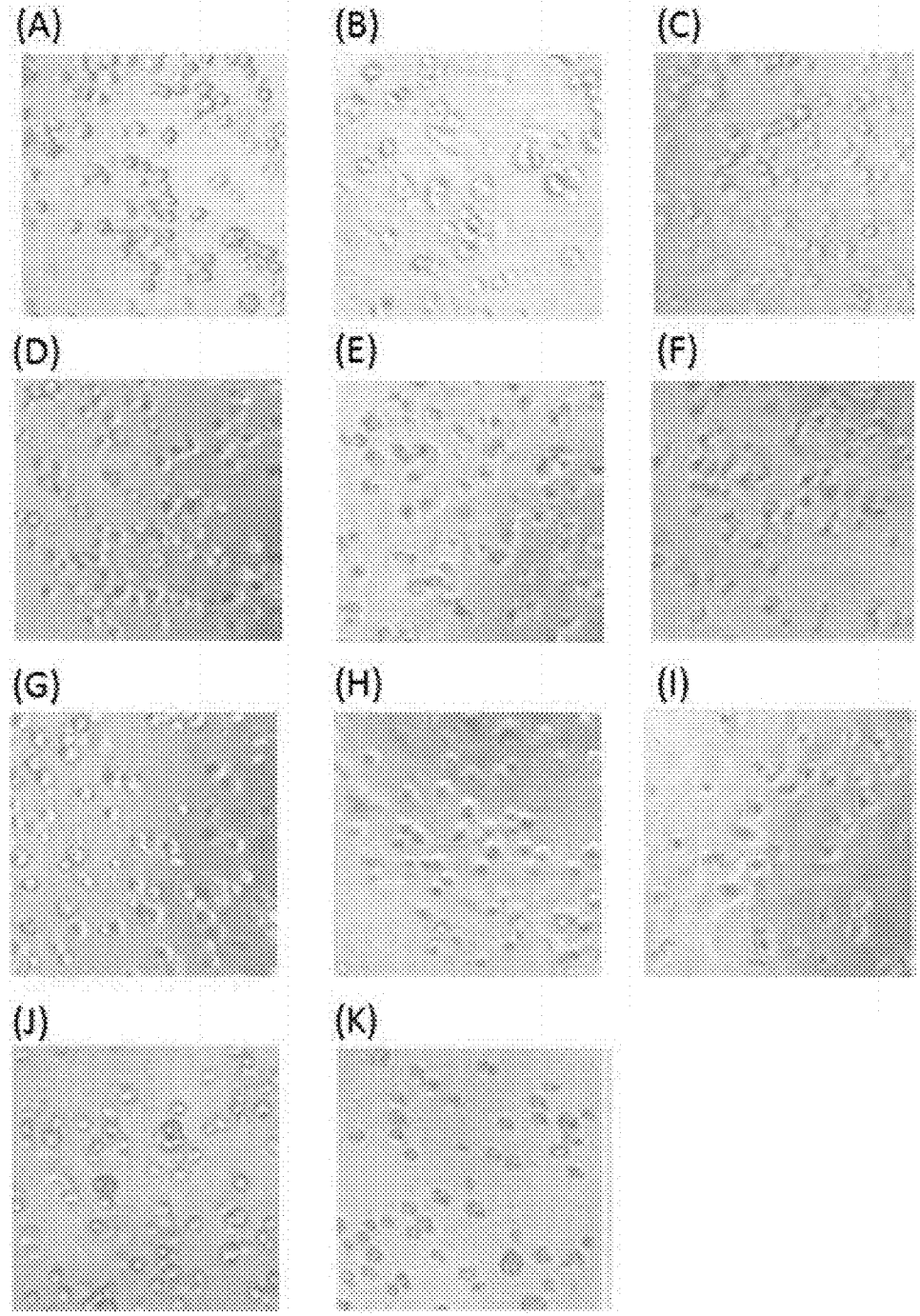

○: the number of bonded cells was 80% or more of the number of bonded unfrozen cells
Δ: the number of bonded cells was 30 to 80% of the number of bonded unfrozen cells
x: the number of bonded cells was 30% or less of the number of bonded unfrozen cells The morphology of the cells of the examples and the comparative examples was observed with a microscope. FIG. 3, (A)-(K) are micrographs showing cell morphology, where (A) is 0.2 wt % SL+30 wt % Gly, (B) is 0.2 wt % SL+20 wt % Gly, (C) is 0.2 wt % SL+15 wt % Gly, (D) is 0.1 wt % SL+30 wt % Gly, (E) is 0.1 wt % SL+20 wt % Gly, (F) is 0.1 wt % SL+15 wt % Gly, (G) is 0.05 wt % SL+30 wt % Gly, (H) is 0.05 wt % SL+20 wt % Gly, (I) is 0.05 wt % SL+15 wt % Gly, (J) is 30 wt % Gly, and (K) is 20 wt % DMSO. The results in Table 17 show that the combination of SL and glycerin is less toxic to mesenchymal stem cells than DMSO. The results in FIGS. 3A to 3K show that more satisfactory cell morphology was obtained by the combination of SL and glycerin than by DMSO.

[11. Effect of SL Addition in Frozen Storage of Vegetables or Fruits]

Aqueous solutions with the compositions shown in Tables 18, 19, and 20 were prepared, and each food (cucumber, spinach, apple) was immersed in 100 g of each aqueous solution for 30 minutes. After immersion, the foods were dried with a paper towel and frozen at −20° C. After overnight storage, the foods were thawed at 37° C. and their appearance and texture were scored according to the following criteria.

(Criteria)
3: No difference from before freezing
2: Different from before freezing
1: Significantly different from before freezing

TABLE 18

|  | Composition | Appearance | Taste | Texture |
|---|---|---|---|---|
| Example 73 | 20 wt % SL | 3.0 | 2.4 | 3.0 |
| Example 74 | 10 wt % SL | 3.0 | 3.0 | 3.0 |
| Example 75 | 5 wt % SL | 3.0 | 3.0 | 3.0 |
| Example 76 | 1 wt % SL | 3.0 | 2.5 | 2.4 |
| Example 77 | 0.1 wt % SL | 3.0 | 2.1 | 1.8 |
| Comparative Example 37 | Water | 3.0 | 1.8 | 1.2 |

TABLE 19

|  | Composition | Appearance | Taste | Texture |
|---|---|---|---|---|
| Example 78 | 10 wt % SL | 3.0 | 3.0 | 3.0 |

TABLE 19-continued

|  | Composition | Appearance | Taste | Texture |
| --- | --- | --- | --- | --- |
| Example 79 | 5 wt % SL | 3.0 | 3.0 | 3.0 |
| Example 80 | 1 wt % SL | 3.0 | 3.0 | 2.8 |
| Example 81 | 0.1 wt % SL | 3.0 | 2.8 | 2.1 |
| Example 82 | 0.01 wt % SL | 3.0 | 2.3 | 1.9 |
| Comparative Example 38 | Water | 3.0 | 1.6 | 1.2 |

TABLE 20

|  | Composition | Appearance | Taste | Texture |
| --- | --- | --- | --- | --- |
| Example 83 | 20 wt % SL | 2.8 | 2.5 | 3.0 |
| Example 84 | 10 wt % SL | 3.0 | 3.0 | 3.0 |
| Example 85 | 1 wt % SL | 3.0 | 3.0 | 2.7 |
| Example 86 | 0.1 wt % SL | 3.0 | 2.6 | 2.0 |
| Comparative Example 39 | Water | 3.0 | 1.8 | 1.4 |

The results in Tables 18, 19, and 20 confirmed that vegetables or fruits immersed in an SL-containing solution before frozen storage had a good taste and texture when thawed after frozen storage.

[12. Effect of SL Addition in Frozen Storage of Seafood or Meat]

Aqueous solutions with the compositions shown in Tables 21 and 22 were prepared, and each food (tuna, liver) was immersed in 100 g of each aqueous solution for 30 minutes. After immersion, the foods were dried with a paper towel, weighed (weight before freezing), and frozen at −20° C. After overnight storage, the foods were thawed at 37° C. Their appearance was observed, and their drip amounts were also measured. The appearance was scored according to the following criteria.

(Criteria)
3: No difference from before freezing
2: Different from before freezing
1: Significantly different from before freezing The drip amount (weight after removal of food) was measured and drip loss was calculated by the following equation. When a food is thawed, ice in its cells melts into water, which flows out of damaged cells. This water is called drip.

Drip loss (%)=drip amount/weight before freezing×100

TABLE 21

|  | Composition | Appearance | Drip Loss (%) |
| --- | --- | --- | --- |
| Example 87 | 20 wt % SL | 2.6 | 16.7 |
| Example 88 | 10 wt % SL | 3.0 | 16.7 |
| Example 89 | 5 wt % SL | 3.0 | 20.1 |
| Comparative Example 40 | Water | 1.8 | 23.4 |

TABLE 22

|  | Composition | Appearance | Drip Loss (%) |
| --- | --- | --- | --- |
| Example 90 | 20 wt % SL | 3.0 | 1.5 |
| Example 91 | 10 wt % SL | 3.0 | 1.8 |
| Example 92 | 5 wt % SL | 3.0 | 2.0 |
| Comparative Example 41 | Water | 2.1 | 2.2 |

The results in Tables 21 and 22 confirmed that immersing seafood or meat in an SL-containing solution before frozen storage reduces drip loss.

What is claimed is:

1. A cell cryopreservation method comprising:
   adding a 1 volume % of a composition comprising 0.01 wt % to 20 wt % of a sophorose lipid to cells in a cell culture medium just before or up to 6 hours before cryopreserving the cells; and
   cryopreserving the cell culture medium, wherein the composition improves cell viability after cryopreservation compared to cells that are cryopreserved with a similar composition that does not contain the sophorose lipid.

2. The method according to claim 1, wherein the composition further comprises 5 wt % to 10 wt % of dimethyl sulfoxide (DMSO).

3. The method according to claim 2, wherein a 10 volume % to 99 volume % of the composition is added to the cells.

4. The method according to claim 1, wherein the composition further comprises 1 wt % to 50 wt % of a polyhydric alcohol.

5. The method of claim 4, wherein the polyhydric alcohol comprises at least one of glycerin, ethylene glycol, and propylene glycol.

6. The method of claim 4, wherein the composition does not contain dimethyl sulfoxide (DMSO).

7. The method of claim 4, wherein the polyhydric alcohol is glycerin, and the cells are stem cells.

8. The method of claim 4, wherein the stem cells are mesenchymal stem cells.

* * * * *